(12) United States Patent
Shinde

(10) Patent No.: US 9,126,916 B2
(45) Date of Patent: *Sep. 8, 2015

(54) METHODS OF CONVERTING MIXTURES OF PALMITOLEIC AND OLEIC ACID ESTERS TO HIGH VALUE PRODUCTS

(71) Applicant: Heliae Development, LLC, Gilbert, AZ (US)

(72) Inventor: Sandip Shinde, Gilbert, AZ (US)

(73) Assignee: Heliae Development, LLC, Gilbert, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/159,370

(22) Filed: Jan. 20, 2014

(65) Prior Publication Data

US 2015/0133693 A1 May 14, 2015

Related U.S. Application Data

(63) Continuation of application No. 13/949,507, filed on Jul. 24, 2013, now Pat. No. 8,642,814.

(60) Provisional application No. 61/675,221, filed on Jul. 24, 2012.

(51) Int. Cl.
| | |
|---|---|
| C07C 45/62 | (2006.01) |
| C07C 67/333 | (2006.01) |
| C07C 209/60 | (2006.01) |
| C07C 45/68 | (2006.01) |
| C07C 45/65 | (2006.01) |
| C07C 67/035 | (2006.01) |
| C07C 67/313 | (2006.01) |

(52) U.S. Cl.
CPC ............... *C07C 45/68* (2013.01); *C07C 45/65* (2013.01); *C07C 67/035* (2013.01); *C07C 67/313* (2013.01)

(58) Field of Classification Search
CPC .... C07C 45/62; C07C 45/455; C07C 67/333; C07C 67/343; C07C 67/475; C07C 209/60
USPC ................ 568/356, 374; 585/502; 554/25, 27
See application file for complete search history.

(56) References Cited

U.S. PATENT DOCUMENTS

| | | | |
|---|---|---|---|
| 4,078,012 | A | 3/1978 | Blewett |
| 5,084,292 | A | 1/1992 | Van Dort |
| 6,057,372 | A | 5/2000 | Nobuhiro |
| 6,200,254 | B1 | 3/2001 | Lupo |
| 6,861,551 | B2 | 3/2005 | Tanabe |
| 7,247,753 | B2 | 7/2007 | Wartini |
| 7,534,917 | B1 | 5/2009 | Ngo |
| 7,812,185 | B2 | 10/2010 | Burdett |
| 7,943,560 | B2 | 5/2011 | Narula |
| 2005/0256341 | A1 | 11/2005 | Wartini |
| 2009/0264672 | A1 | 10/2009 | Abraham |
| 2010/0120643 | A1 | 5/2010 | Brown |

FOREIGN PATENT DOCUMENTS

| | | |
|---|---|---|
| EP | 1264594 A2 | 12/2002 |
| WO | 2012061093 | 5/2012 |
| WO | 2012061095 | 5/2012 |
| WO | 2014018578 | 1/2014 |

OTHER PUBLICATIONS

Alamu et al., "Effect of Ethanol-palm Kernel Oil Ratio on Alkali-catalyzed Biodiesel Yield," Fuel, 87, 2008, pp. 1529-1533.
Blomquist et al., "Many Membered Carbon Rings. II. A New Synthesis of Civetone and dl-Muscone," Jan. 1948, vol. 70, pp. 34-36.
Burdett et al., "Renewable Monomer Feedstocks via Olefin Metathesis: Fundamental Mechanistic Studies of Methyl Oleate Ethenolysis with the First-Generation Grubbs Catalyst," Organometallics, 2004, vol. 23, No. 9, pp. 2027-2047.
Chikkali et al., "Refining of Plant Oils to Chemicals by Olefin Methathesis," Agnew. Chem. Int. Ed., 2012, 51, pp. 2-9.
Choo, et al., "Synthesis of Civetone from Palm Oil Products," JAOCS, vol. 71, No. 8, Aug. 1994, pp. 911-913.
Dinger et al., "High Turnover Numbers with Ruthenium-Based Metathesis Catalysts, Advanced Synthesis & Catalysis," Adv. Synth. Catal., Apr. 2002, 344, No. 6+7, pp. 671-677.
Duangyod et al., "Quantitative Analysis of Civetone and Normuscone in Secretion from *Viverricula indica* and in Aromatic Remedies by Gas Chromatography-mass Spectrometry," Journal of Chemical and Pharmaceutical Research, 2011, 3(5), pp. 196-204.
Encinar et al., "Biodiesel Fuels from Vegetable Oils: Transesterification of *Cynara cardunculus* L. Oils with Ethanol," Energy & Fuels, 2002, 16, pp. 443-450.
Fjerbaek et al., "A Review of the Current State of Biodiesel Production Using Enzymatic Transesterification," Biotechnology and Bioengineering, Apr. 2009, vol. 102, No. 5, pp. 1298-1315.
Fortineau et al., "Chemistry Perfumes Your Daily Life," Journal of Chemical Education, Jan. 2004, vol. 81, No. 1, pp. 45-50.
Furstner, et al., "Ring Closing Alkyne Metathesis: Stereoselective Synthesis of Civetone," Journal of Organonmetallic Chemistry, 2000, 606, pp. 75-78.
Hamasaki et al., "A Highly Efficient Synthesis of Civetone," Tetrahedron, 56, 2000, pp. 7423-7425.
International Search Report and Written Opinion of the International Searching Authority for International Application No. PCT/US2013/051753, mailing date of Nov. 14, 2013, 10 pages.
Kraft et al., "Odds and Trends: Recent Developments in the Chemistry of Odorants," Angew. Chem. Int. Ed. 2000, 39, pp. 2980-3010, 31 pages.
Liu et al., "Transesterification of Soybean Oil to Biodiesel Using CaO as a Solid Base Catalyst," Fuel, 87, 2008, pp. 216-221.
Maguire et al., "Fatty Acid Profile, Tocopherol, Squalene and Phytosterol Content of Walnuts, Almonds, Peanuts, Hazelnuts and the Macadamia Nut," International Journal of Food Sciences and Nutrition, vol. 55, No. 3, May 2004, pp. 171-178.

(Continued)

*Primary Examiner* — Sikarl Witherspoon
(74) *Attorney, Agent, or Firm* — Tom Gallegos, Esq.; Justin Kniep, Esq.; Frank Rosenberg, Esq.

(57) ABSTRACT

The invention describes methods and systems for making particular organic compounds from unsaturated fatty acids derived from biological materials. Particular embodiments describe synthesizing civetone and olefins from a mixture of palmitoleic and oleic unsaturated fatty acid esters. The inventive methods use reaction steps such as metathesis, cyclization, hydrolysis, and/or decarboxylation.

5 Claims, 10 Drawing Sheets

(56) References Cited

OTHER PUBLICATIONS

Marvey et al., "Ruthenium Carbene Mediated Metathesis of Oleate-type Fatty Compounds," International Journal of Molecular Sciences, ISSN 1422-0067, 2008, 9(4), pp. 615-625.

Mata et al., "Biodiesel Production from Corn Oil via Enzymatic Catalysis with Ethanol," Energy Fuels, 2012, 8 pages.

McGinty et al., "Fragrance Material Review on Cylcoheptadecda-9-en-1-one," Food and Chemical Technology, 2011, 49, pp. S93-S97.

Meier et al., "Methathesis with Oleochemicals: New Approaches for the Synthesis of Monomers and Polymers from Renewable Resources," University of Potsdam, 23 pages, retrieved from http://www.meier-michael.com, date unknown.

Meier et al., "Methathesis with Oleochemicals: New Approaches for the Utilization of Plant Oils as Renewable Resources in Polymer Science," Macromolecular Chemistry and Physics, 2009, 210(13-14), pp. 1073-1079.

Modi et al., "Lipase-mediated Conversion of Vegetable Oils into Biodiesel Using Ethyl Acetate as Acyl Acceptor," Bioresource Technology, 98, 2007, pp. 1260-1264.

Mol, "Application of Olefin Metathesis in Oleochemistry: An Example of Green Chemistry," Green Chemistry, 2002, 4, pp. 5-13.

Mol, et al., "Methathesis in Oleochemistry," J. Braz. Chem. Soc., 1998, vol. 9, No. 1, 11 pages.

Moore, "Synthesis and Fragrance Properties of Macrocyclic Musks," Apr. 2005, 8 pages.

Ngo et al., "Methathesis of Unsaturated Fatty Acids: Synthesis of Long-chain Unsaturated-a, É-dicarboxylic Acids," JAOCS, 2006, vol. 83, No. 7, pp. 629-634.

Ngo et al., "Synthesis of Long Chain Unsaturated-a, E-dicarboxylic Acids from Renewable Materials via Olefin Metathesis," J. Amer. Oil Chem. Soc., 2007, 84, pp. 777-784.

Nguyen et al. "Metabolic Engineering of Seeds Can Achieve Levels of Omega-7 Fatty Acids Comparable with the Highest Levels Found in Natural Plant Sources," Plant Physiology, Dec. 2010, vol. 154, pp. 1897-1904.

Park et al., "Low Pressure Ethenolysis of Renewable Methyl Oleate in a Microchemical System," Organic Letters, 2011, vol. 13, No. 9, pp. 2398-2401.

Peters, "Phthalates and Artificial Musks in Perfume," TNO-report, R&I-A R 2005/011, TNO Environment and Geosciences, Jan. 2005, 30 pages.

Ravi et al., "Macrocyclic Musk Compounds: Synthetic Approaches to Key Intermediates for Exaltodlide, Exaltone and Dilactones," J. Indian Inst. Sco., May-Jun. 2001, 81, pp. 299-312.

Rimkus, "Polycyclic Musk Fragrances in the Aquatic Environment," Toxicology Letters, 111, 1999, pp. 37-56.

Rimkus et al., "Musk Xylene and Musk Ketone Amino Metabolites in the Aquatic Environment," Toxicology Letters, 111, 1999, pp. 5-15.

Rossi et al., "Optimization of Molecular Distillation to Concentrate ethyl Esters of Eicosapentaenoic (20:5É-3) and Docosahexaenoic Acids (22:6 É-3) using Simplified Phenomenological Modeling," J. Sci. Food Agric., 2011, 91, pp. 1452-1458.

Rüsch et al., "A Palmitoleic Acid Ester Concentrate from Seabuckthorn Pomace," Eur. J. Lipid Sci. Technol., 106, 2004, pp. 412-416.

Tanabe et al., "Practical Synthesis of (Z)-Civetone Utilizing Ti-Dieckmann Condensation," Adv. Synth. Catal., Apr. 2002, 344, No. 5, pp. 507-510.

Tenllado et al., "A Combined Procedure of Supercritical Fluid Extraction and Molecular Distillation for the Purification of alkylglycerols from Shark Liver Oil," Separation and Purification Technology, 83, 2011, pp. 74-81.

Thomas et al., "Highly Selective Ruthenium Metathesis Catalysts for Ethenolysis," Journal of the American Chemical Society, 2011, 133, pp. 7490-7496.

Tsuji et al., "Application of Olefin Metathesis to Organic Synthesis. Syntheses of Civetone and Macrolides," Tetrahedron Letters, 1980, vol. 21, pp. 2955-2958.

Tsuji et al., "Metathesis Reactions of Unsaturated Esters Catalyzed by Homogeneous Tungsten Complexes. Synthesis of Civetone and Macrolides," Journal of Organometallic Chemistry, 1981, 218, pp. 69-80.

Turk, "Flavor and Fragrance Company," 44 pages.

Turner et al., "A Review of U.S. Patents in the Field of Organic Process Development Published during Mar. and Apr. 2005," Organic Process Research & Development, Jun. 2005, vol. 9, No. 4, pp. 386-396.

Wille et al., "Palmitoleic Acid Isomer (C16:1delta6) in Human Skin Sebum is Effective Against Gram-Positive Bacteria," Skin Pharmacology and Applied Skin Physiology, 2003, 16, 3, pp. 176-187, retrieved from http://www.ncbi.nlm.nih.gov/pubmed/12677098, Abstract Only, 2 pages.

Yang et al., "Fatty Acid Composition of Lipids in Sea Buckthorne (*Hippophaë rhamnoides* L.) Berries of Different Origins," J. Agric. Food Chem., 2001, 49, pp. 1939-1947.

Zabeti et al., "Activity of Solid Catalysts for Biodiesel Production: A Review," Fuel Processing Technology, 90, 2009, pp. 770-777.

METHODS OF CONVERTING MIXTURES OF PALMITOLEIC AND OLEIC ACID ESTERS TO HIGH VALUE PRODUCTS

RELATED APPLICATIONS

This application is a continuation of U.S. patent application Ser. No. 13/949,507, filed 24 Jul. 2013, now U.S. Pat. No. 8,642,814. This application claims priority to U.S. Provisional Application No. 61/675,221 filed 24 Jul. 2012.

INTRODUCTION

Currently, most chemical production is based on petrochemical feedstocks (also known as fossil fuels). These feedstocks are obtained from carbon sources that have been buried underground for millions of years. These petrochemical feedstocks are being extracted from their underground repositories and converted into a myriad of chemicals for uses ranging from fuel to plastics to commodity chemicals to high value compounds such as fragrances. Although techniques for modifying petrochemical feedstocks are very well developed, there are serious drawbacks from petrochemical-based technologies including declining supplies of petrochemicals and environmental hazards in extracting the petrochemicals from underground repositories. In addition, much of the carbon from the petrochemicals ends up in the atmosphere in the form of carbon monoxide (CO) and carbon dioxide ($CO_2$) which are implicated in global warming.

To ameliorate the problems with petrochemicals, great efforts have been expended in developing alternatives to petrochemical-based technologies. One such alternative to petrochemical feedstocks are carbon-containing compounds extracted from recently-living organisms. As organisms such as algae and plants grow, they extract $CO_2$ from the atmosphere, thus providing a major advantage over fossil fuel technology. A challenge with using these organisms to replace fossil fuels is the relative cost of growing them and making useful products from these organisms. Thus, there has been a long-standing problem of increasing the value of products obtained from living or recently-living organisms such as algae and plants. This invention provides new techniques for making high-value products from mixtures of palmitoleic acid esters and oleic acid esters that are derived from biological materials.

As described in greater detail below, the invention provides a new route to civetone and olefinic co-products. Civetone is a macrocyclic ketone which is used as an ingredient in perfume and fragrance products. In nature, civetone is a pheromone produced by the African Civet. Due to the limited natural supply, methods of synthesizing civetone have been developed. Known sources of starting materials for synthesizing civetone include compositions high in oleic acid (C18:1; $C_{18}H_{34}O_2$), such as palm oil, and compositions high in aleuritic acid ($C_{16}H_{32}O_5$), such as shellac. The current methods for synthesizing civetone have not achieved a high efficiency, with the overall isolated yields for known methods of synthesizing civetone from oleic acid ranging from 23-74% in lab settings and yields from aleuritic acid being even lower. The ability to get higher overall yields of selected products is an advantage of some preferred embodiments of the invention.

Civetone can be synthesized from Omega-7 rich oil, such as, but not limited to, the commonly known sources sea buckthorn and macadamia nut oil. The monounsaturated fatty composition (C16:1 and C18:1) for Sea buckthorn is around 50% (Yang & Kallio, 2001) and for Macadamia nut oil (Maguire, O'Sullivan, Galvin, O'Connor, & O'Brien, 2004) it is approximately 80%. In the present invention, ethyl esters of Palmitoleic acid (C16:1) and Oleic acid (C18:1) obtained from Omega-7 rich oil sources can be used as precursors for synthesis of civetone.

Synthesis of ethyl esters is known for the enrichment of Omega-3 fatty acids. Transesterification of Omega-7 fatty acids to produce ethyl esters can be done using multiple catalyst/conditions, such as the following catalyst/conditions:

a) enzymatic (Fjerbaek, Christensen, & Norddahl, 2009) (Modi, Reddy, Rao, & Prasad, 2007)(Mata, Sousa, Vieira, & Caetano, 2012);

b) acid/base catalyzed (Rodri & Tejedor, 2002)(Alamu, Waheed, & Jekayinfa, 2008); or c) heterogeneous catalyst (Zabeti, Wan Daud, & Aroua, 2009)(Liu, He, Wang, Zhu, & Piao, 2008).

As shown in FIG. 1, ethyl esters of Omega-7 oil can be separated using one or more separation techniques, such as, but not limited to, molecular distillation. Molecular distillation is a separation technique used for separation of fatty acid methyl esters (FAME) in biodiesel production process. Ethyl esters from Omega-7 rich oil can be separated into three fractions (Rossi, Pramparo, Gaich, Grosso, & Nepote, 2011) (Tenllado, Reglero, & Torres, 2011):

1) Fuel (such as C10 to C16)
2) Omega-7 (such as C16:1 and C18:1)
3) Omega-3 fractions (such as C20:5 and C22:6).

After molecular distillation, the fuel fraction can provide feed to a hydrotreater for synthesis of high cetane diesel through hydrodeoxygenation treatments known in the art. The high cetane diesel produced may be isomerized, using methods known in the art, to give jet fuel. The omega-7 fraction (mono-saturated fatty acids), composed of Palmitoleic acid (C16:1) and Oleic acid (C18:1), is a commercial product with many potential uses in the health industry. Omega-7 (Palmitoleic acid) is found in human skin sebum and is known to decline with age (Wille & Kydonieus, 2003). Omega 7 supplements comprising sea buckthorn oil are currently available in the market as a health product for skin and hair (contains approximately 30% Omega 7)(Yang & Kallio, 2001). Omega 7 ethyl esters can substitute for sea buckthorn oil in products, and provide an advantage due to the fact that esters can provide a higher purity not currently available in the market (Rüsch gen. Klaas & Meurer, 2004). In preferred embodiments of the present invention, the Omega-7 rich fraction is used for synthesis of civetone by olefin metathesis.

PRIOR ART

Prior Art: Known method of synthesizing civetone from palm oil

In 1994 (Choo, Ooi, & Ooi, 1994), synthesis of Civetone was reported from Palm oil. In this process Oleic acid (C18:1) was obtained from Palm oil by hydrolytic splitting with 99% purity. See FIG. 2. The pure Oleic acid was esterified under acidic conditions using concentrated sulfuric acid at 110° C. Self-metathesis of ethyl oleate was performed using $WCl_6$ and $SnMe_4$ to give two products, 9-Octadecene and Diethyl 9-Octadecenedioate, with almost quantitative yields of 97 and 99% respectively. Silica-gel chromatography was used to separate the two products. The Diethyl 9-Octadecenedioate was cyclized using base catalyzed Dieckmann Condensation under inert conditions. Dieckmann Condensation was carried out under argon using potassium hydride (KH) in dry THF at 55° C. for 3 hours to give 2-ethoxycarbonyl-9-cycloheptadecenone with 63% yield which was purified by silica-gel chromatography. Civetone was synthesized by hydrolysis followed by decarboxylation of 2-ethoxycarbonyl-9-cycloheptadecenone using 5% NaOH/THF/Ethanol with 93% yield which was also purified by silica-gel chromatography.

Prior Art: Known methods of ethenolysis of methyl oleate and synthesis of civetone using methyl 9-decenoate Ethenolysis of Methyl Oleate In 2011, ethenolysis of methyl oleate (Thomas, Keitz, Champagne, & Grubbs, 2011) was performed using N-Aryl, N-alkyl N-heterocyclic carbene (NHC) ruthenium metathesis catalysts with 95% selectivity for terminal olefins.

Ethenolysis of methyl oleate can be performed using First Generation Grubb's catalyst (Burdett et al., 2004) or in a microbial system (Park, Van Wingerden, Han, Kim, & Grubbs, 2011) to give 1-Decene and Methyl 9-Decenoate as products. See FIG. 3.

Synthesis of Civetone Using Methyl 9-Decenoate

In 2000, Ti-Claisen condensation of Methyl 9-Decenoate followed by an intramolecular metathesis reaction was used for synthesis of civetone (Hamasaki, Funakoshi, Misaki, & Tanabe, 2000). See FIG. 4.

Ti-Claisen condensation of Methyl 9-Decenoate was carried using $TiCl_4$ and $Bu_3N$ at 0-5° C. for 1 hour to give β-ketoester as a product with 93% yield. The β-ketoester was then allowed to undergo intramolecular metathesis using Grubb's reagent at 110° C. to give 2-methoxycarbonyl-9-cycloheptadecenone with 84% yield. The intermediate 2-methoxycarbonyl-9-cycloheptadecenone gives Civetone after hydrolysis followed by decarboxylation with 95% yield.

SUMMARY

The invention describes certain naturally-derived (bio-based) products and systems and methods for synthesizing civetone and other products from an omega-7 containing composition. The term "bio-based" or "naturally-derived" means that the compounds are synthesized from recently-living biological materials rather than petrochemical feedstocks. In this way, the compounds and methods offer a significant advantage over petro-based components in that they remove carbon from the atmosphere. Practically, bio-based materials can be distinguished from petrochemical-based materials by the well known techniques of $^{14}C$ dating. Bio-based materials will have significant levels of $^{14}C$ that are typical of biological material that was living within the past few hundred years. In contrast, petro-based compounds will have essentially zero $^{14}C$.

In a first aspect (see FIG. 5), the invention provides a method of converting a mixture comprising derivatives of palmitoleic acid and oleic acid to useful products including olefinic hydrocarbons, comprising: reacting a composition comprising an ester of palmitoleic acid and an ester of oleic acid in a metathesis reaction to produce a first reaction mixture; reacting at least a portion of the first reaction mixture, or derivatives thereof, in a cyclization reaction to produce a second reaction mixture; hydrolyzing and decarboxylating at least a portion of the second reaction mixture, or derivatives thereof, to produce a third reaction mixture comprising civetone. The phrase "or derivatives thereof" means that the reaction mixtures can be modified by treatments, such as transesterifications, that do not have a significant deleterious effect on subsequent synthesis steps. This method yields civetone along with at least one olefinic compound selected from the group of Olefin D ($C_{14}H_{28}$ see FIG. 6), and Olefin C ($C_{16}H_{32}$ see FIG. 6), and 1-Octene ($C_8H_{16}$). In practice, of course, any of the reaction co-products can be separated or used as intermediates in further reactions—products that are separated or consumed as intermediates in a further reaction are still included in calculations of yield and selectivity.

The "esters" referred to are generally made by esterification or transesterification of precursor composition comprising palmitoleic acid and oleic acid. A preferred precursor composition comprises a mixture of palmitoleic acid C16:1 ($C_{16}H_{30}O_2$) and oleic acid C18:1 ($C_{18}H_{34}O_2$), which is a mixture that can be obtained in an extract from sources such as algae, sea buckthorn, and macademia. In one preferred embodiment, the precursor composition is derived from algae.

In some preferred embodiments, the esters are produced by esterification or transesterification in the presence of a catalyst such as an enzymatic, acidic, basic, and/or heterogeneous catalyst. In some embodiments the esters comprise methyl esters or ethyl esters.

In some of the inventive aspects, the invention can be further characterized one or more of any of the following: the palmitoleic acid and oleic acid are present in the precursor composition in at least 50 mass % as a percentage of the total mass of unsaturated fatty acids, in some embodiments, at least 80%, and in some embodiments at least 90% as a percentage of the total mass of unsaturated fatty acids. Likewise, the composition of esters preferably contains at least 50 mass % (in some embodiments at least 80%, or at least 90%) of C16 palmitoleic-acid-derived esters and C18 oleic-acid-derived esters as a mass percentage of all fatty acid esters present in the composition. The mass percent of palmitoleic acid (or the corresponding esters) as a percent of the sum of palmitoleic acid plus oleic acid (or the corresponding esters) is preferably in the range of 20 to 80%, in some embodiments 30 to 70%, in some embodiments 40 to 60%, in some embodiments, 20 to 50%, in some embodiments 50 to 80%. These characteristics can be present individually or in combination.

In some embodiments, the precursor composition or composition comprises about equal parts palmitoleic acid and oleic acid or (in the composition) their corresponding fatty acid esters (i.e., each is within the range of 45 to 55% of their total mass). In some embodiments, the precursor composition or composition comprises a greater portion of palmitoleic acid (or esters) than oleic acid (or esters). In some embodiments, the composition comprises a greater portion of oleic acid ester(s) than palmitoleic acid ester(s). In some preferred embodiments, the C16 and C18 fatty acids or corresponding esters in the precursor composition or composition comprises at least 50 mass % (absolute) of the total mass of the precursor composition or composition, in some embodiments at least 70% or at least 80%, and in some embodiments up to 99% or 100%.

At any stage of the method, selected products can be separated or purified by known methods; for example, silica gel chromatography or HPLC. The invention includes any of the products or reaction mixtures in purified form. For example, any of the chemical compounds can be obtained in forms that are at least 50 mass % pure (i.e., no more than 50 mass % of components other than those listed in a claim). For example, if a mixture is described as "comprising 1-octene, 1-decene, and ethyl 9-decenoate," then the invention also includes (in more specific embodiments) a mixture comprising at least 50 mass % of 1-octene, 1-decene, and ethyl 9-decenoate. Likewise, the invention includes compositions comprising at least 50 mass % of any of the specific products and intermediates described herein, since it is contemplated that any of the products or intermediates can be isolated. In some preferred embodiments, any of the compounds or mixtures are at least 80% (by mass) pure, in some embodiments at least 99% pure.

In some embodiments, the metathesis reaction is a self-metathesis reaction producing a reaction mixture comprising $C_{18}H_{36}$, $C_{14}H_{28}$, and $C_{22}H_{40}O_4$. In some embodiments, the metathesis reaction is a cross-metathesis reaction producing a reaction mixture comprising $C_{16}H_{32}$ and $C_{22}H_{40}O_4$. In some embodiments, the metathesis reaction comprises a catalytic system selected from the group consisting of: $WCl_6/Me_4Sn$; Heterogeneous $Re_2O_7/Al_2O_3$ (rhenium oxide on alumina); Heterogeneous $Re_2O_7/SiO_2.Al_2O_3/SnBu4$; $W(O-2,6-C_6H_3X_2)2Cl_4$ (X=Cl, Ph) precatalysts promoted with $Me_4Sn$; $B_2O_3.Re_2O_7/Al_2O_3.SiO_2/SnBu_4$; $WCl_6$ and $WOCl_4$, as primary catalysts and $SnMe_4$, $PbMe_4$, $Cp_2TiMe_2$, and $Cp_2ZrMe_2$, as cocatalysts; Ruthenium based catalyst; Grubb's catalyst first generation; Grubbs catalyst second generation; and Hoveyda-Grubbs catalyst. In some preferred embodiments, the metathesis catalyst comprises rhenium oxide, preferably supported on alumina or an aluminosilicate.

In some embodiments, the cyclization reaction comprises Dieckmann condensation. In some embodiments, the cyclization reaction is carried out with metal hydrides under inert conditions. In some embodiments, the cyclization reaction is carried out with $TiO_2$ doped with alkali or alkaline earth metal oxides in gaseous phase reaction. In some embodiments, the cyclization reaction comprises Ti-Dieckmann or Ti-Claisen condensation.

In some embodiments, civetone is extracted from the product mixture using ether. In further embodiments, the extracted civetone can be further purified, for example, by using silica-gel chromatography. In some embodiments, the Ti-Dieckmann cyclization forms a reaction mixture comprising 34-membered macrocyclic ketones. In some embodiments, the method includes a hydrogenation reaction of the $C_{22}H_{40}O_4$ to produce a reaction mixture and followed by a cyclization step to produce dihydrocivetone (cycloheptadecanone).

In another embodiment, fatty acid esters of palmitoleic acid and oleic acid are reacted with ethene to produce a reaction mixture; and subsequently reacting at least a portion of this reaction mixture (or a derivative thereof) in a condensation reaction; and then conducting a second metathesis reaction, followed by hydrolysis and decarboxylation to produce civetone and 1-Octene ($C_8H_{16}$).

In some embodiments, the metathesis reaction with ethene produces a mixture comprising 1-Octene ($C_8H_{16}$), 1-Decene ($C_{10}H_{20}$), and ethyl 9-decenoate ($C_{12}H_{22}O_2$). In some embodiments the condensation reaction is a Ti-Claisen condensation with a catalysis system selected from the group consisting of: $TiCl_4$—$Bu_3N$, Pentafluorophenylammonium Triflate, and $MgBr_2.OEt_2$ in DIPEA. In some embodiments, the metathesis reaction of the condensation produces ethene and a macrocyclic compound. In some embodiments, the macrocylcic compound is 2-ethoxycarbonyl-9-cycloheptadecenone. In some preferred embodiments, the ethene produced is recycled to the step of reacting the esters in a metathesis reaction with ethene. In some embodiments, the condensation product comprises a beta-ketoester. In further embodiments, the beta-ketoester can be purified, for example by extraction ether and optional additional steps such as chromatography, for example, silica-gel chromatography.

In further aspects of the invention, the invention provides a method of producing olefins. In this method, fatty acid esters of the unsaturated fatty acids C16:1 ($C_{16}H_{30}O_2$) and C18:1 ($C_{18}H_{34}O_2$) are reacted in a metathesis reaction to produce a reaction mixture comprising $C_{18}H_{36}$, $C_{14}H_{28}$, $C_{16}H_{32}$ and $C_{22}H_{40}O_4$. The invention also includes compositions that comprise a mixture of the biobased olefins Olefin E ($C_{18}H_{36}$ see FIG. 6), Olefin D ($C_{14}H_{28}$ see FIG. 6), and Olefin C ($C_{16}H_{32}$ see FIG. 6). The invention further includes compositions comprising the individual biobased Olefin C, Olefin D and mixtures thereof, made by methods of the present invention. In some preferred embodiments the composition comprises at least 10% of Olefin C or Olefin D as a percentage of all olefins in a composition; in some embodiments at least and 10% of Olefin C and at least 10% Olefin D; in some embodiments at least 20% of Olefin C or Olefin D; at least 20% of Olefin C and at least 20% of Olefin D; in some embodiments, 5% to 50% of Olefin C; in some embodiments 5% to 50% of Olefin D; all as a percentage of the total mass of olefins in the composition. In some preferred embodiments, the composition comprises at least 5 mass % of olefins; at least 10 mass % olefins; at least 20 mass % olefins; or at least 50 mass % based on total mass of the composition. In each case, the olefins are biobased which is a significant advantage over petrochemical derived olefins. The compositions can be used in the synthesis of polymers or chemical compounds, and can be used as a fuel additive, for example, to increase octane rating.

In any of its aspects, the invention may also be characterized by yields. In each case, yield is calculated based on carbon in the selected product or intermediate and in the monounsaturated fatty acid esters present in a starting material composition. In the reactions carried out using metathesis of the palmitoleic and oleic acid esters, the yield of Diester F (see FIG. 6 below) is preferably greater than 20%, more preferably at least 30%, in some embodiments in the range of 30 to about 60%, and in some embodiments 40 to 55%. In the reactions carried out using metathesis of the palmitoleic and oleic acid esters, the yield of the sum of Olefins C, D, and E (see FIG. 6 below) is preferably at least 20%, more preferably at least 30%, in some embodiments 30 to 44%, in some embodiments 35 to 43%, and in some embodiments 38 to 43%. In some embodiments, the yield of Olefin C is at least 5%, in some embodiments at least 10%, in some embodiments, at least 15%, in some embodiments in the range of 10% to 20%. In some embodiments, the yield of Olefin D is at least 5%, in some embodiments at least 10%, in some embodiments, at least 15%, in some embodiments at least 20%, in some embodiments at least 25%, in some embodiments in the range of 10% to about 38%, in some embodiments in the range of 10% to 30%, in some embodiments in the range of 15% to 25%. Note that, using the above definition of yield, in the noninventive case of pure oleic acid ester as the starting material, the maximum theoretical yields of Diester F and Olefin E would be 55 and 45%, respectively. For the cyclization of Diester F, the yield of cyclized intermediate is preferably at least 60%, in some embodiments in the range of 60 to 95%. For the combined steps of hydrolysis and decarboxylation the yield of civetone is preferably at least 60%, in some embodiments in the range of 60 to 95%.

In the reactions carried out using metathesis with ethene, the yield of ethyl 9-decenoate is preferably at least 30%, more preferably at least 40%, in some embodiments in the range of 30 to about 65%, in some embodiments 35 to 60% (carbon in ethyl 9-decenoate divided by carbon in starting materials. Note that, using the present carbon-based definition, for the noninventive case of pure oleic acid the maximum theoretical yield of ethyl 9-decenoate is 55%. The yield of 1-octene is preferably at least 5%, in some embodiments at least 10%, in some embodiments at least 15%, in some embodiments at least 20%, in some embodiments in the range of 10 to 40%, in some embodiments 10 to 35%, in some embodiments 15 to 30%. The yield of 1-decene is preferably at least 5%, in some embodiments at least 10%, in some embodiments at least 15%, in some embodiments at least 20%, in some embodiments in the range of 10 to 40%, in some embodiments 10 to 35%, in some embodiments 15 to 30%. The yield of the condensation of ethyl 9-decenoate is preferably at least 60%, in some embodiments 60 to 95%. The yield of the cyclized compound from metathesis of the beta-ketoester is civetone is preferably at least 60%, in some embodiments in the range of 60 to 95%. For the combined steps of hydrolysis and decarboxylation the yield of civetone is preferably at least 60%, in some embodiments in the range of 60 to 95%.

In preferred embodiments, the invention has an overall yield, based on carbon in the products (civetone plus olefinic hydrocarbons) divided by the sum of carbon in the palmitoleic acid ester and oleic acid ester starting materials of greater than 25%, preferably greater than 50%, preferably greater than 60%, in some embodiments in the range of 40% to 80%, in some embodiments greater than 60% to 95%, in some embodiments greater than 60% to 85%, in some embodiments at least 70%, in some embodiments 75 to 90%.

In another aspect, the invention provides a method of producing α-olefins, comprising: producing esters from an composition comprising at least 50 mass % of palmitoleic acid and oleic acid; and reacting at least a portion of the esters in a metathesis reaction with ethene to produce a reaction mixture comprising 1-Octene ($C_8H_{16}$), 1-Decene ($C_{10}H_{20}$), and ethyl 9-decenoate ($C_{12}H_{22}O_2$).

In yet another aspect, the invention provides a method of synthesizing dihydrocivetone. In this method, civetone is made as described herein and then hydrogenated to produce dihydrocivetone.

In yet another aspect, the invention provides a method of synthesizing cyclopropanated civetone. In this method, civetone is made as described herein and then reacted in a Simmons-Smith reaction using ZnCu and $CH_2I_2$ to produce cyclopropanated civetone.

In still further embodiments, certain melanin production inhibitors (described herein) are produced. In some embodiments, an acyloin condensation of diethyl 9-octadecenedioate produces a 2-hydroxy macrocyclic ketones which is subsequently converted to melanin production inhibitors. In some embodiments, reducing civetone produces melanin production inhibitors. The reduction may include hydrogenation to make civetol.

In various embodiments, the invention can provide advantages such as: the production of civetone and other high value products from algae-derived products; greater efficiency in fully utilizing starting materials; the ability to make valuable products such as olefins, polyolefins, and precursors for lubricants, olefins, polymers, and plasticizers; and the synthesis of environmentally-friendly, biobased olefins.

As is standard patent terminology, the term "comprising" means "including" and permits the presence of additional components. Where the invention is characterized as "comprising" it should be understand that the invention, in narrower embodiments, can alternatively be characterized as "consisting essentially of" or "consisting of" in place of "comprising." Such language limits the invention to the named components plus components that do not materially degrade the properties of the invention, or narrow the invention to only the stated components, respectively. In the descriptions of the invention, the phrase "such as" should be understood as not limiting but only providing some non-limiting examples.

DETAILED DESCRIPTION

In some preferred embodiments, a mixture comprising Palmitoleic acid (C16:1) and Oleic acid (C18:1) is used as a precursor for synthesis of Civetone. Preferably, the mixture of palmitoleic acid and oleic acid is obtained by transesterification of an Omega-7 rich oil followed by molecular distillation and is termed "the Omega-7 rich fraction".

Figure 1:
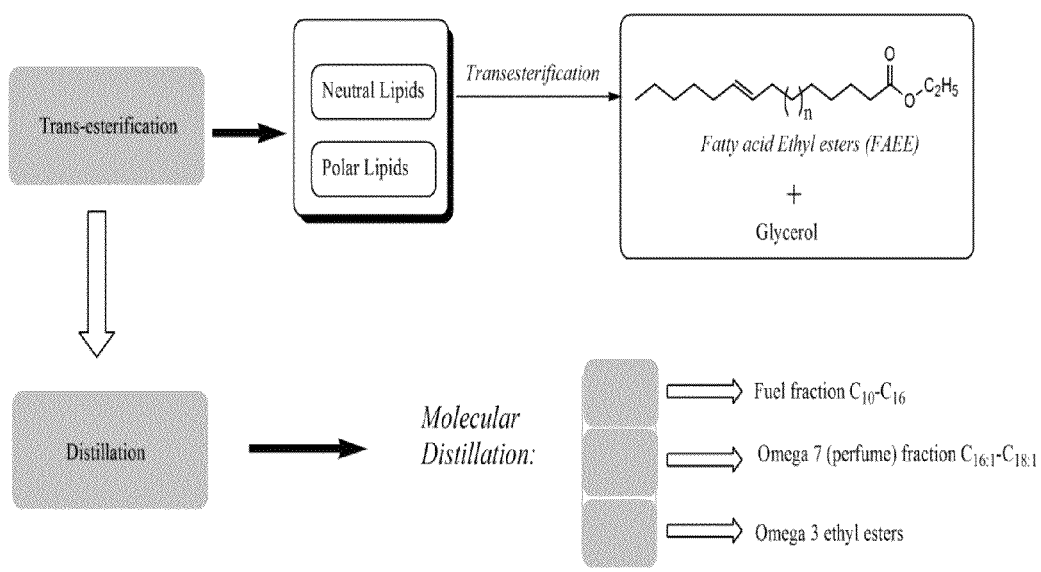
FIG. 1 illustrates examples of synthesis of esters from oil and separation into fractions based on fatty acid chain length.
Figure 2:
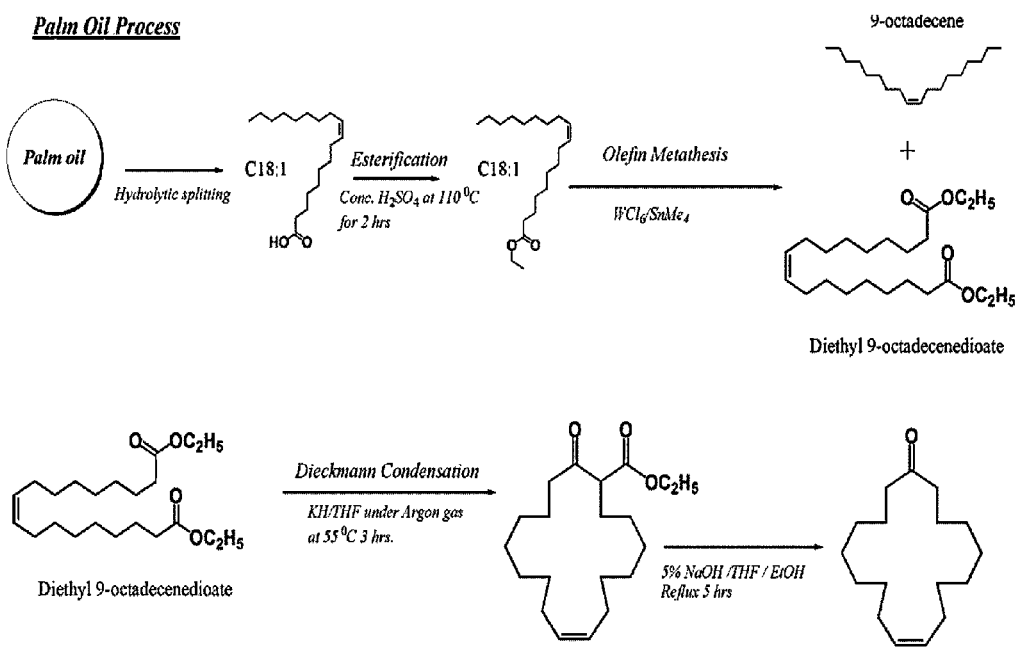
FIG. 2 illustrates a known method of synthesizing civetone from palm oil.
Figure 3:
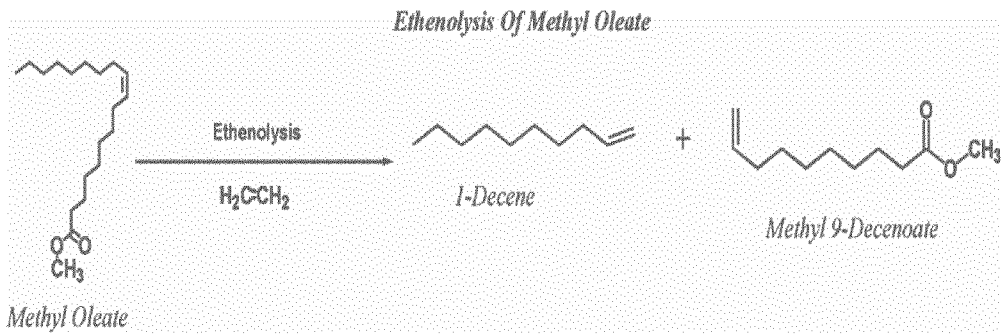
FIG. 3 illustrates a known method for the ethenolysis of methyl oleate.
Figure 4:
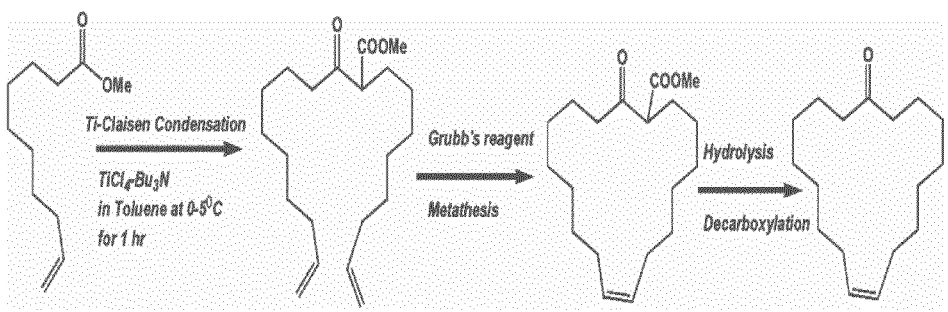
FIG. 4 illustrates a known method of synthesizing civetone from methyl 9-decenoate.
Figure 5:
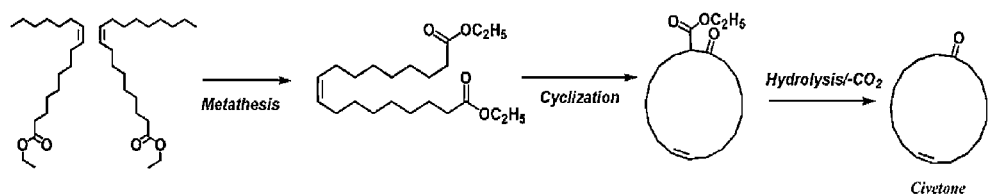
FIG. 5 illustrates a method for synthesizing civetone
Figure 6:
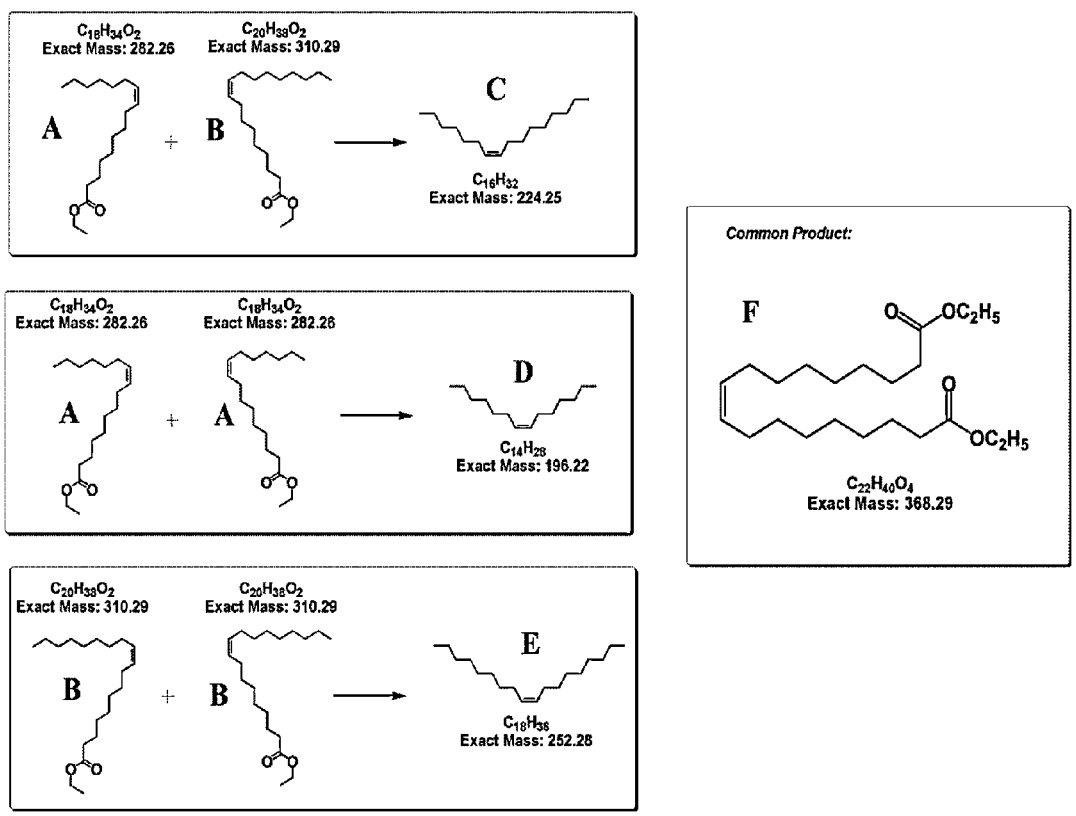
FIG. 6 illustrates products produced in the Metathesis of Palmitoleic acid and Oleic acid.

Metathesis of Palmitoleic Acid and Oleic Acid:

Methathesis:

A fraction of fatty acids that can be obtained from biomaterials such as algae or plants is a mixture of ethyl esters Palmitoleic acid (C16:1) and Oleic acid (C18:1). The metathesis of this composition will produce a unique mixture of products, not available through prior art methods. Referring to FIG. 6, the Omega 7 fraction self-metathesis of the Palmitoleic acid ester (A) will yield olefin (D), and Diethyl ester (F) as products. The products will also include self-metathesis products of the Oleic acid esters (B), which are olefin (E) and Diethyl ester (F). The Omega 7 fraction will also undergo a cross metathesis reaction between the Palmitoleic acid ester (A) and the Oleic acid ester (B) to give olefin (C), a product not available through prior art methods, and Diethyl ester (F).

Figure 7:
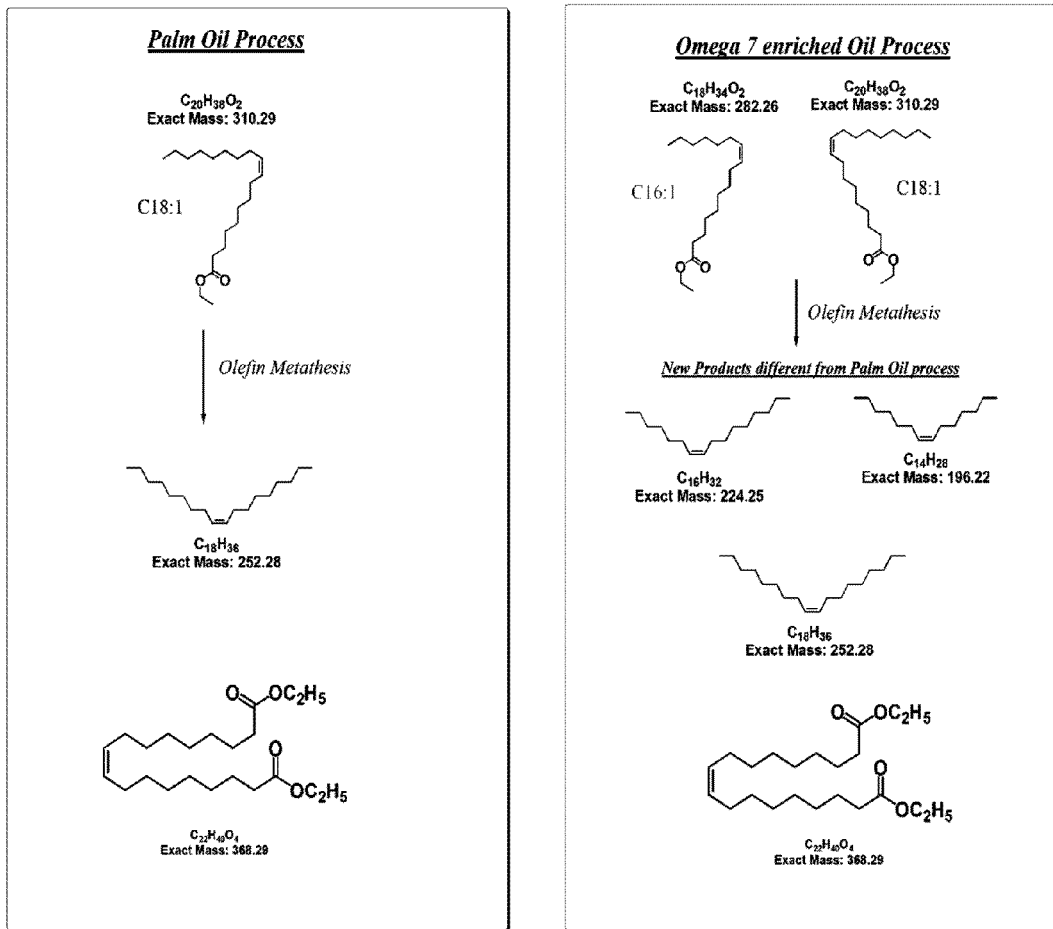
FIG. 7 is a side-by-side comparison of metathesis stage of a prior art process of synthesizing civetone from palm oil (left) and the invention method (1) of synthesizing civetone and new polyolefin products from Omega-7 rich oil (right).

The Palmitoleic acid of the Omega-7 rich fraction is derived from sources such as sea buckthorn and macadamia oil, but not palm oil. Therefore the olefin metathesis reaction of the Omega-7 rich oil will give unique products which are not obtainable by the prior art methods comprising olefin metathesis of ethyl oleate obtained from palm oil, as shown in FIG. 7.

Cyclization:

The diethyl ester (product F in FIG. 6) produced from the metathesis stage can be cyclized using Dieckmann condensation or its variant.

Dieckmann condensation:

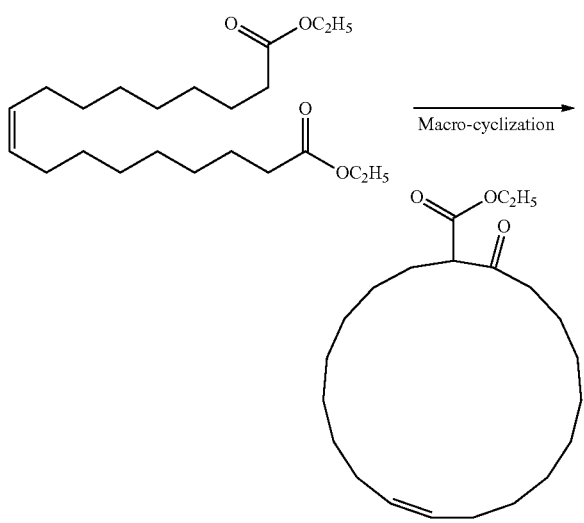

Hydrolysis and Decarboxylation:

The cyclized compound can be hydrolyzed and decarboxylated to form civetone.

Synthesis of Civetone

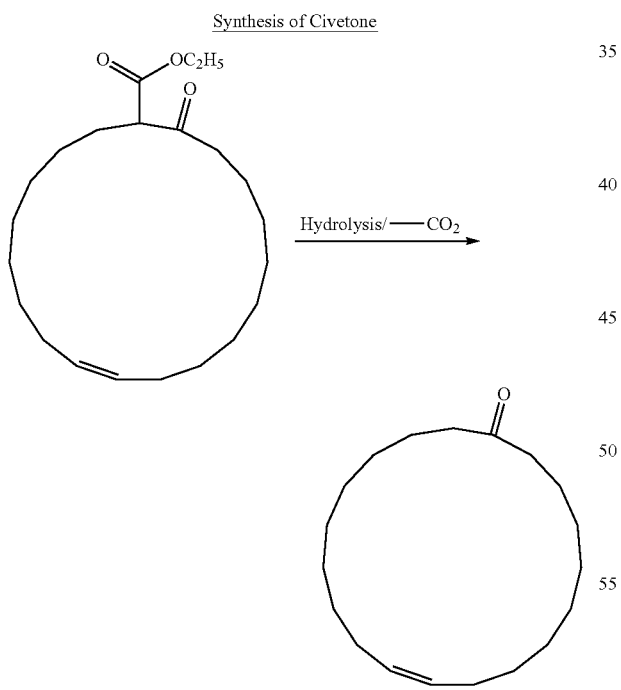

Figure 8:
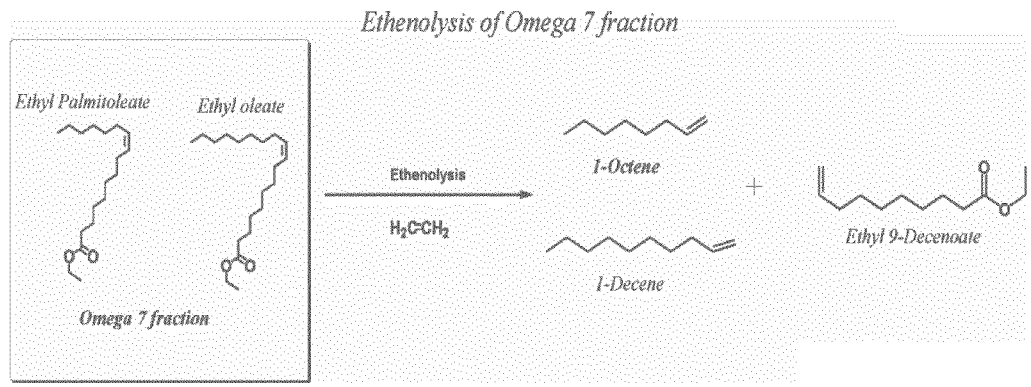
FIG. 8 illustrates ethenolysis of a mixture of ethyl esters of Palmitoleic acid (C16:1) and Oleic acid (C18:1).
Figure 9:
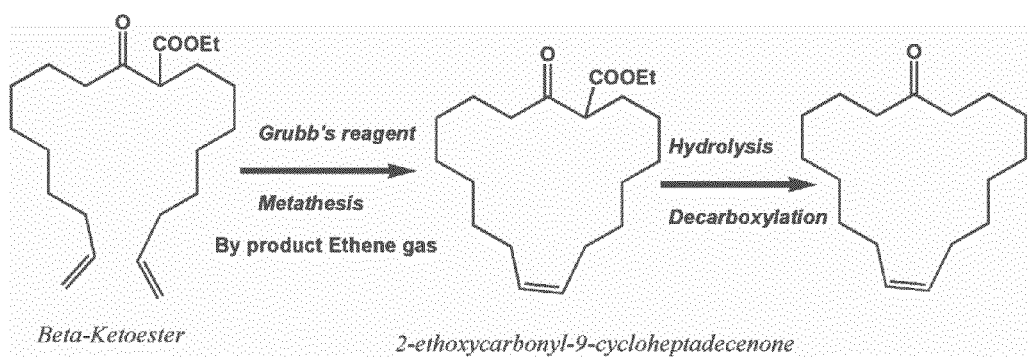
FIG. 9 illustrates metathesis, hydrolyzation, and decarboxylation to make civetone.

Ethenolysis:

Ethenolysis comprises a cross-metathesis reaction involving ethene. According to some preferred embodiments of the invention, a mixture of ethyl esters of Palmitoleic acid (C16:1) and Oleic acid (C18:1) are subjected to conditions of ethenolysis to yield a mixture of α-olefins (1-Octene and 1-Decene) and Methyl 9-Decenoate. See FIG. 8. The 1-Octene is a product unique to ethenolysis of Palmitoleic acid (C16:1). In the inventive method, Ethyl 9-Decenoate and 1-Decene will also form from the mixture of Palmitoleic and Oleic acid ethyl esters. Prior art methods using Oleic acid esters (Methyl Oleate) as the starting material only produce Methyl 9-Decenoate and 1-Decene.

Condensation:

The Ethyl 9-Decanoate (see above) can be subjected to a Claisen condensation.

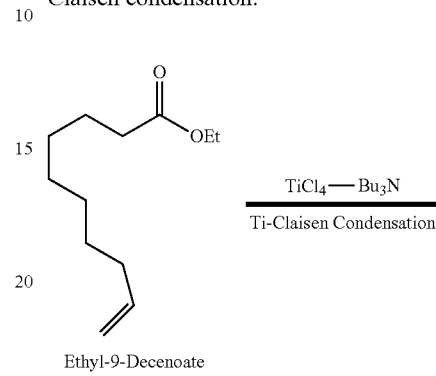

Ethyl-9-Decenoate

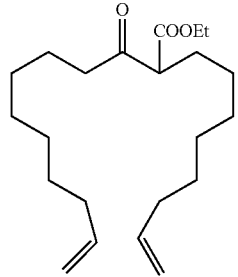

Beta-ketoester

Intramolecular Metathesis:

The product of the condensation stage can be subjected to an intramolecular metathesis reaction to produce ethane gas and a macrocyclic compound, such as 2-ethoxycarbonyl-9-cycloheptadecenone. The ethene gas can be recycled to the ethenolysis step for use in the ethenolysis reaction.

Hydrolyization and Decarboxylation:

The macrocyclic beta-ketoester compound can be hydrolyzed and decarboxylated to form civetone.

Examples

Contemplated

Invention Embodiment 1 Example

Metathesis of Omega-7 Fraction

Figure 10:
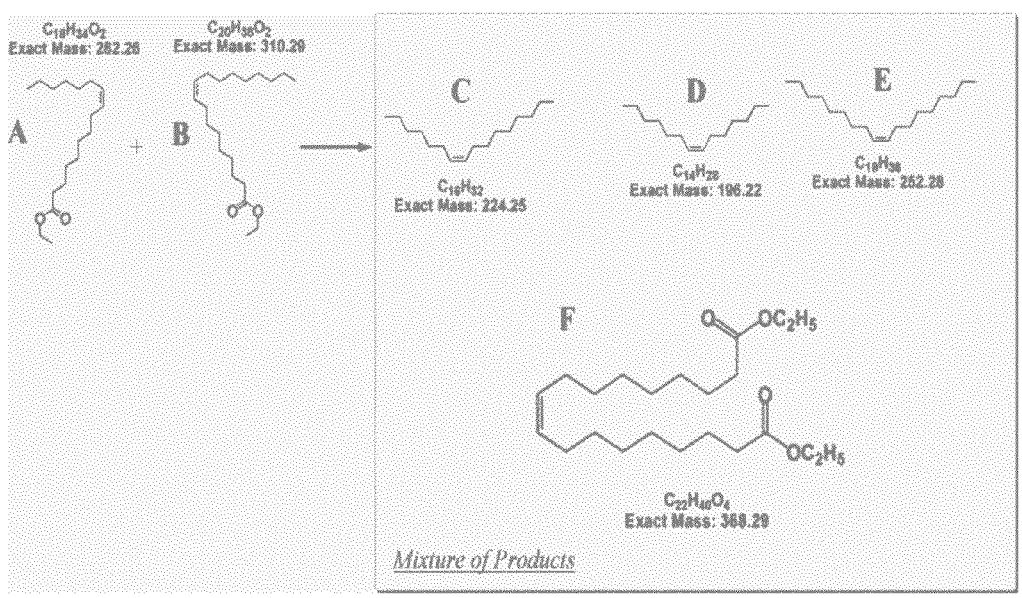
FIG. 10 illustrates products from metathesis reactions of Omega-7 fraction in invention method 1.

The 2$^{nd}$ generation ruthenium catalyst (IMesH$_2$)(PCy$_3$)(Cl)$_2$Ru=CHPh where IMesH$_2$ is 1,3-dimesityl-4,5-di-hydroimidazol-2-ylidene with its bulky N-heterocyclic carbine (NHC) ligand (Dinger & Mol, 2002) is known to perform with high turnover numbers and gives the product with high selectivity and can be an ideal catalyst for metathesis of Omega-7 fraction. The reaction will be carried out in inert atmosphere at about 55° C. The products Diethyl 9-Octadecenedioate and mixture of olefins formed in this reaction will be purified by silica-gel chromatography. See FIG. 10.

Metathesis Catalysts:

In oleochemistry, olefin metathesis is well known and it includes self-metathesis (SM), cross-metathesis (CM), ring closing metathesis (RCM), ring-opening metathesis (ROM) and ROM polymerization (ROMP) as well as acyclic diene metathesis polymerization (ADMET) reactions. A variety of catalytic systems can be utilized for metathesis of Omega-7 fraction to achieve selectivity and high turnover numbers, such as:

- WCl$_6$/Heterogeneous Re$_2$O$_7$/A$_{l2O3}$
- Heterogeneous Re$_2$O$_7$/SiO$_2$.Al$_2$O$_3$/SnBu$_4$
- W(O-2,6-C$_6$H$_3$X$_2$)2Cl$_4$ (X=Cl, Ph) precatalysts promoted with Me$_4$Sn
- B$_2$O$_3$.Re$_2$O$_7$/Al$_2$O$_3$.SiO$_2$/SnBu$_4$
- WCl$_6$ and WOCl$_4$, as primary catalysts and SnMe$_4$, PbMe$_4$, Cp$_2$TiMe$_2$, and Cp$_2$ZrMe$_2$, as cocatalysts,
- Ruthenium based catalysts (Grubb's catalyst first, second generation and Hoveyda-Grubbs catalyst).

Table 1 illustrates examples of catalysts which can be used to perform metathesis of the omega-7 fraction (Mol, 2002).

TABLE 1

Examples of catalyst system for metathesis of (m)ethyl oleate

| Catalyst | Ester/metal atom$^a$ | T/° C. | t$^b$/h | TON$^c$ | Ref. |
|---|---|---|---|---|---|
| Homogeneous systems | | | | | |
| WCl$_4$/Me$_4$Sn | 75 | 110 | 2 | 38 | 26 |
| W(OC$_6$H$_3$Cl$_2$-2,6)$_2$Cl$_4$/Bu$_4$Pb | 50 | 85 | 0.5 | 25 | 30 |
| W(=CHCMe$_3$)NpCl(OAr)$_2$(OEt$_2$)$^d$ | 100 | 85 | 1 | 32 | 31 |
| [W]=CHCMe$_3$ (see formula I) | 300 | 25 | 2-3 | 150 | 32 |
| [W]=CHCMe$_3$ (see formula II) | 500 | 25 | 1 | 250 | 33 |
| Ru(=CH—CH=CPh$_2$)Cl$_2$(PCy$_3$)$_2$ | 2 000 | 20 | 96 | 960 | 34 |
| Ru(=CHPh)Cl$_2$(PCy$_3$)$_2$ | 5 500 | 20 | 48 | 2 500 | 35 |
| [Ru$_2$]=CHPh(III, R' = CF$_3$) | 550 | 40 | 1 | 225 | 36 |
| Ru(=CHPh)Cl$_2$(H$_2$IMes)(PCy$_3$) (IV)$^e$ | 987 000 | 55 | 6 | 440 000 | 48 |
| Heterogeneous systems | | | | | |
| Re$_2$O$_7$/Al$_2$O$_3$/Et$_4$Sn | 60 | 20 | 2 | 3 | 18 |
| Re$_2$O$_7$/MoO$_3$/Al$_2$O$_3$/Et$_4$Sn | 60 | 20 | 2 | 30 | 18 |
| Re$_2$O$_7$/B$_2$O$_3$/Al$_2$O$_3$/Bu$_4$Sn | 120 | 20 | 2 | 50 | 37 |
| Re$_2$O$_7$/SiO$_2$—Al$_2$O$_3$/Bu$_4$Sn | 240 | 40 | 2 | 120 | 10 |
| Re$_2$O$_7$/B$_2$O$_3$/SiO$_2$—Al$_2$O$_3$/Bu$_4$Sn$^f$ | 480 | 20 | 2 | 160 | 38 |
| Re$_2$O$_7$/B$_2$O$_3$/SiO$_2$—Al$_2$O$_3$/Bu$_4$Sn$^g$ | 200 | 80 | 2 | 99 | 39 |
| CH$_3$ReO$_3$/SiO$_2$—Al$_2$O$_3$ | 100 | 25 | 2 | 27 | 40 |
| MoO$_3$/SiO$_2$/(CO, hv)/cyclopropane | 250 | 50 | 0.17 | 25 | 41 |
| MoO$_3$/SiO$_2$/(CO, laser)/cyclopropane | 1 250 | 40 | 3 | 500 | 10 |

$^a$Molar ratio.
$^b$t = Time to reach the highest conversion.
$^c$TON = Moles of substrate converted per mol of W, Ru, Re or Mo into reaction products.
$^d$Ar = C$_6$H$_3$Ph$_2$-2,6; Np = CH$_2$CMe$_3$.
$^e$No solvent.
$^f$Silica-alumina containing ~25 wt % Al$_2$O$_3$.
$^g$Silica-alumina containing 60 wt % Al$_2$O$_3$.

Dieckmann Condensation (Macrocyclization):

Dieckmann condensation:

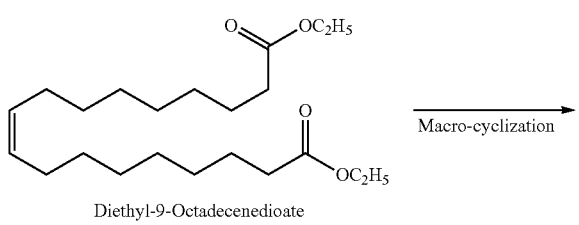

Diethyl-9-Octadecenedioate  →(Macro-cyclization)

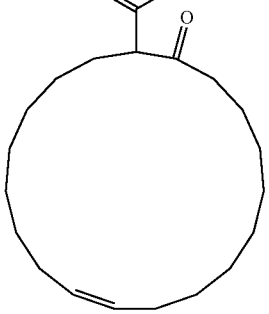

2-ethoxycarbonyl-9-cycloheptadecenone

Ti-Dieckmann (intramolecular Ti-Claisen) condensation (Hamasaki et al., 2000; Tanabe, Makita, Funakoshi, Hamasaki, & Kawakusu, 2002a; "U.S. Pat. No. 6,861,551.pdf," n.d.) (TiCl$_4$/amine) will be used to cyclize Diethyl 9-Octadecenedioate. The reaction will be carried out at around 0-5° C. for about 1 hour to give the cyclized product 2-ethoxycarbonyl-9-cycloheptadecenone which can be purified by silica-gel chromatography. The same macro cyclization (Dieckmann condensation) can be carried out in different conditions:

- KH or NaH (metal hydrides) under inert conditions.
- TiO$_2$ doped with alkali or alkaline earth metal oxides (Na$_2$O or K$_2$O) in gaseous phase reaction.
- ZrCl$_4$/Bu$_3$N similar to Ti-Dieckmann condensation.

Hydrolysis and Decarboxylation:

2-ethoxycarbonyl-9-cycloheptadecenone will be refluxed with about 10% NaOH in methanol for about 1 hour to give civetone. After completion of the reaction, the reaction mixture will be neutralized using about 10% sulfuric acid. The product will be extracted using ether and can be purified using silica-gel chromatography.

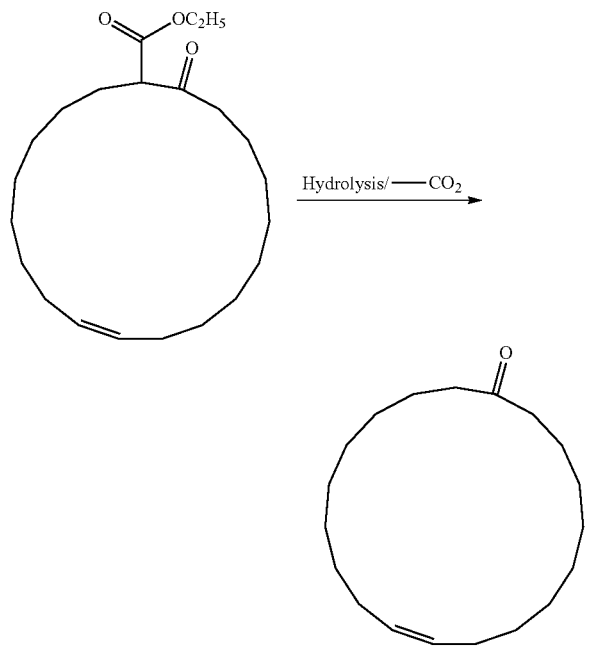

Hydrolysis and Decarboxylation to Form Civetone

Invention Embodiment 2 Example

Ethenolysis of Omega-7 Fraction

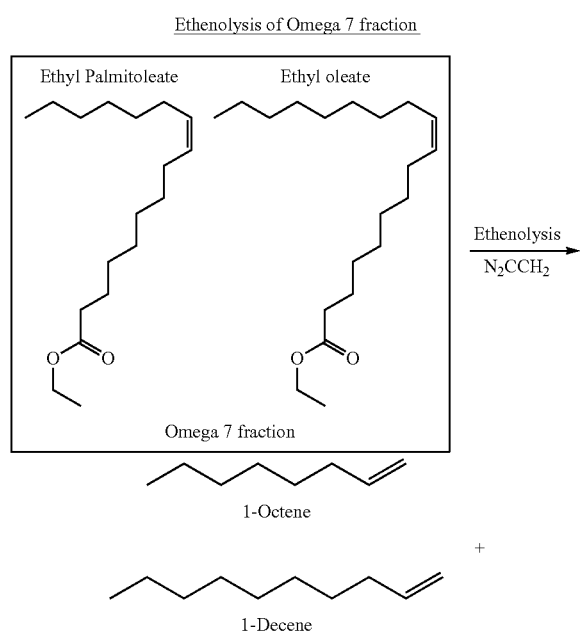

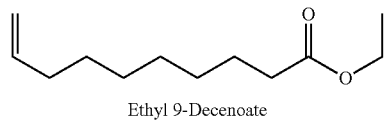

Ethyl 9-Decenoate

Ethenolysis Reaction of Omega 7 Fraction

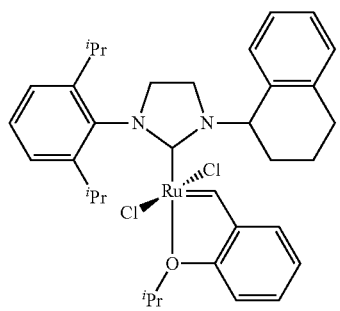

A

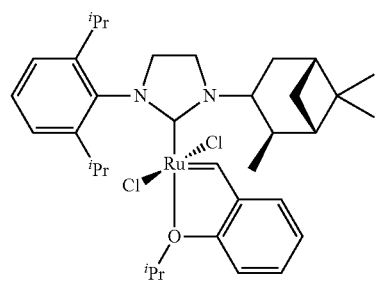

B

Catalysts for Use in Ethenolysis Reaction of Omega 7 Fraction

Ethenolysis of the Omega-7 fraction will be carried out under inert atmosphere with ethylene under conditions of about 150 psi pressure and about 40° C. (Thomas et al., 2011). N-Aryl,N-alkyl N-heterocyclic carbene (NHC) ruthenium metathesis catalysts are highly selective toward the ethenolysis of methyl oleate. The catalysts shown in FIG. 16, (A) and (B), give more kinetic selectivity when catalyst loading was ≈500 ppm due to their sterically demanding ligands. Catalyst A-88% selectivity with 78% yield while catalyst B with 88% selectivity and 77% yield. The products will be separated using silica gel chromatography.

Similar to the Invention embodiment 1 example, a metathesis reaction can be performed by selecting a catalyst from a variety of metathesis catalysts (Table 1).

Ti-Claisen Condensation of Ethyl-9-Decenoate:

Ti-Claisen condensation (Hamasaki et al., 2000) will be performed by adding $TiCl_4$ to mixture of $Bu_3N$ and Ethyl decenoate at around 0-5° C. The reaction mixture will be stirred for approximately 1 hour and then will be quenched by the addition of water. The product β-ketoester will be extracted using ether and will be purified by silica-gel chromatography.

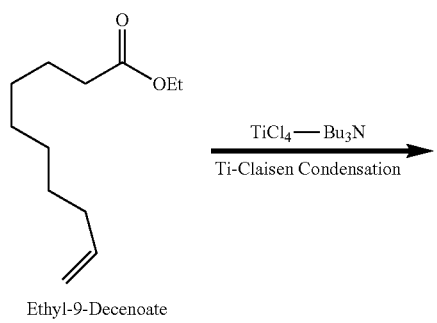

Ethyl-9-Decenoate

TiCl₄—Bu₃N
Ti-Claisen Condensation

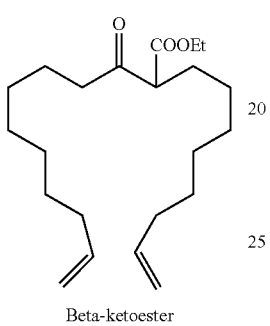

Beta-ketoester

Intramolecular Metathesis Reaction, Hydrolysis and Decarboxylation:

The intramolecular metathesis reaction will be similar to the Invention embodiment 1 example metathesis reaction of an Omega-7 fraction. The metathesis reaction can be carried out with a selected catalyst as described above. The hydrolysis and decarboxylation will be carried out as described above.

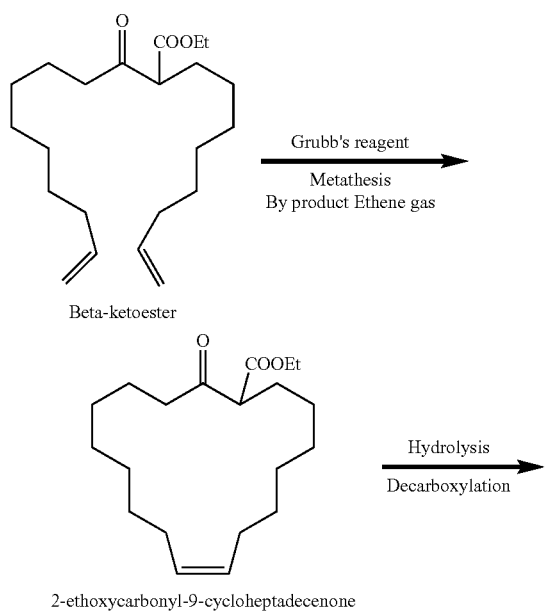

Beta-ketoester

Grubb's reagent
Metathesis
By product Ethene gas

Hydrolysis
Decarboxylation 2-ethoxycarbonyl-9-cycloheptadecenone

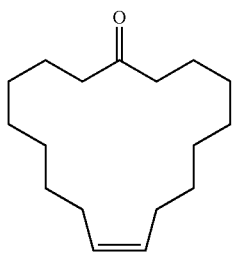

Additional Embodiments

Potential Products from Invention Methods of Synthesizing Civetone Relevant to Perfume Industry (Macrocyclic Ketone)

The Invention methods disclosed above for synthesizing civetone will give geometrical isomers of the final product which are Cis-Civetone and Trans-Civetone.

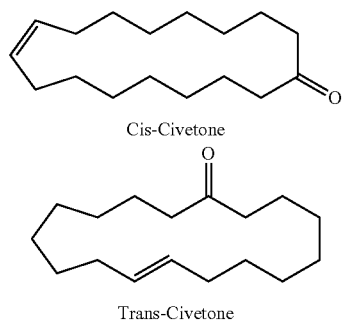

Cis-Civetone

Trans-Civetone

Invention embodiment 1 cyclization mediated Ti-Dieckmann conditions (Tanabe, Makita, Funakoshi, Hamasaki, & Kawakusu, 2002a) will predominately give Z-isomer of Civetone with approximately 50% yield. Invention embodiment 2 intramolecular metathesis will give a mixture of E:Z (3:1) isomers of Civetone with 90% yield (Hamasaki et al., 2000).

Ti-Dieckmann cyclization conditions may lead to the formation of 34-membered macrocyclic ketones, which have potential uses in the perfume industry. The 34-membered macrocycle can be formed using TiCl₄-Et₃N, with approximately 14% yield (Tanabe, Makita, Funakoshi, Hamasaki, & Kawakusu, 2002b).

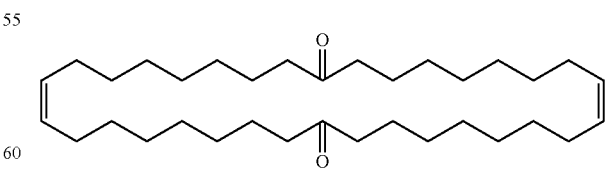

Dihydrocivetone (Cycloheptadecanone) is another macrocyclic ketone with musk fragrance and can be synthesized by hydrogenation of the final product (Civetone) or by hydrogenation of Diethyl 9-Octadecenedioate followed by cyclization.

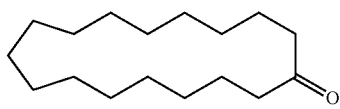 [SMILES: O=C1CCCCCCCCCCCCCCCC1]

In 2011 International Flavors & Fragrances Inc. introduced a new class of chemical entities cyclopropanated macrocycles (see U.S. Pat. No. 7,943,560) as flavors and fragrances. Civetone (both geometrical isomers) can undergo Simmons-Smith reaction using ZnCu and $CH_2I_2$ to give cyclopropanated Civetone.

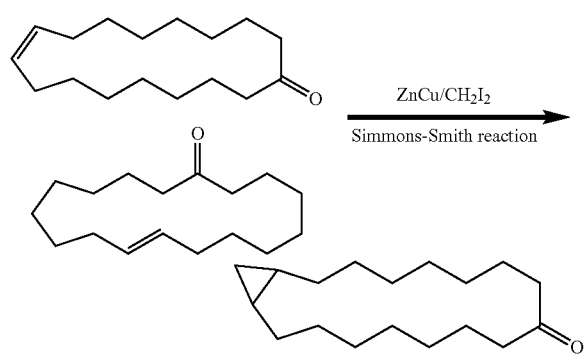

Figure 11:
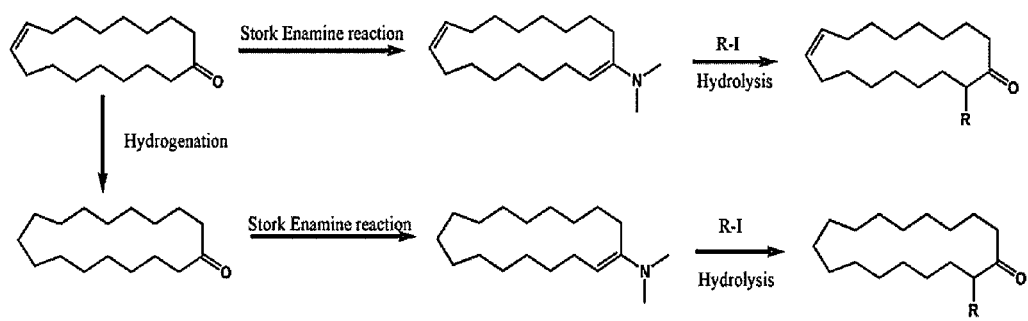
FIG. 11 illustrates alkylation of civetone macrocycle.

Alkylation:

Muscone (3-Methyl cyclopentadecanone) is methylated macrocycle with musk fragrance. Civetone macrocycle can be alkylated (methylated) to give 2-methyl 9-Cycloheptadecen-1-one which can be potential product for perfume industry. Alkylation reaction can be done using Stork enamine conditions to substitute the macrocycles with different alkyl groups. See FIG. 11.

Figure 12:
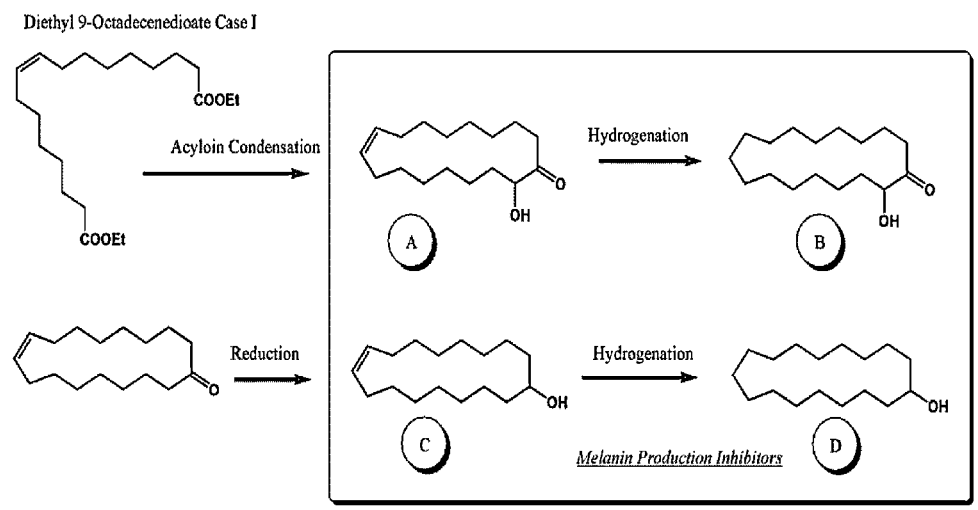
FIG. 12 illustrates the synthesis of melanin-production-inhibiting products from the acyloin condensation of civetone.

Macrocycles with Potential Melanin Production Inhibition Activity which can be Used in Skin Care Products ("Melanin Production Inhibitors," n.d.):

Diethyl 9-Octadecenedioate product from Invention embodiment 1 can undergo Acyloin condensation to give 2-hydroxy macrocyclic ketones, which can inhibit Melanin production, as shown in FIG. 12. Civetone can be reduced to give product C, which is a potential melanin production inhibitor, and hydrogenation of Product C gives Civetol D.

LITERATURE

Alamu, O. J., Waheed, M. a., & Jekayinfa, S. O. (2008). Effect of ethanol-palm kernel oil ratio on alkali-catalyzed biodiesel yield. *Fuel*, 87(8-9), 1529-1533. doi:10.1016/j.fuel.2007.08.011

Burdett, K. a., Harris, L. D., Margl, P., Maughon, B. R., Mokhtar-Zadeh, T., Saucier, P. C., & Wasserman, E. P. (2004). Renewable Monomer Feedstocks via Olefin Metathesis: Fundamental Mechanistic Studies of Methyl Oleate Ethenolysis with the First-Generation Grubbs Catalyst. *Organometallics*, 23(9), 2027-2047. doi:10.1021/om0341799

Choo, Y.-may, Ooi, K. E., & Ooi, I.-hong. (1994). Synthesis of Civetone from Palm Oil Products, 71(8), 911-913.

Dinger, M. B., & Mol, J. C. (2002). High Turnover Numbers with Ruthenium-Based Metathesis Catalysts. *Advanced Synthesis & Catalysis*, 344(6-7), 671. doi:10.1002/1615-4169(200208)344:6/7<671::AID-ADSC671>3.0.00; 2-G Fjerbaek, L., Christensen, K. V., & Norddahl, B. (2009). A review of the current state of biodiesel production using enzymatic transesterification. *Biotechnology and bioengineering*, 102(5), 1298-315. doi:10.1002/bit.22256

Hamasaki, R., Funakoshi, S., Misaki, T., & Tanabe, Y. (2000). A Highly Efficient Synthesis of Civetone, 56, 7423-7425.

Holley, W., & Spencer, R. D. (1948). Many-membered Carbon Rings. 11. A New Synthesis of Civetone and dl-Muscone, 30(10), 34-36.

Liu, X., He, H., Wang, Y., Zhu, S., & Piao, X. (2008). Transesterification of soybean oil to biodiesel using CaO as a solid base catalyst. *Fuel*, 87(2), 216-221. doi:10.1016/j.fuel.2007.04.013

Maguire, L. S., O'Sullivan, S. M., Galvin, K., O'Connor, T. P., & O'Brien, N. M. (2004). Fatty acid profile, tocopherol, squalene and phytosterol content of walnuts, almonds, peanuts, hazelnuts and the macadamia nut. *International journal of food sciences and nutrition*, 55(3), 171-8. doi:10.1080/09637480410001725175

Mata, T. M., Sousa, I. R. B. G., Vieira, S. S., & Caetano, N. S. (2012). Biodiesel Production from Corn Oil via Enzymatic Catalysis with Ethanol. *Energy & Fuels*, 120427072504002. doi:10.1021/ef300319f Melanin Production Inhibitors. (n.d.).

Modi, M. K., Reddy, J. R. C., Rao, B. V. S. K., & Prasad, R. B. N. (2007). Lipase-mediated conversion of vegetable oils into biodiesel using ethyl acetate as acyl acceptor. *Bioresource technology*, 98(6), 1260-4. doi:10.1016/j.biortech.2006.05.006

Mol, J. C. (2002). Application of olefin metathesis in oleochemistry: an example of green chemistry. *Green Chemistry*, 4(1), 5-13. doi:10.1039/b109896a Park, C. P., Van Wingerden, M. M., Han, S.-Y., Kim, D.-P., & Grubbs, R. H. (2011). Low pressure ethenolysis of renewable methyl oleate in a microchemical system. *Organic letters*, 13(9), 2398-401. doi:10.1021/ol200634y Rodri, J. J., & Tejedor, A. (2002). Biodiesel Fuels from Vegetable Oils: Transesterification of Cynara cardunculus L. Oils with Ethanol, (7), 443-450.

Rossi, P. C., Pramparo, M. D. C., Gaich, M. C., Grosso, N. R., & Nepote, V. (2011). Optimization of molecular distillation to concentrate ethyl esters of eicosapentaenoic (20:5 ω-3) and docosahexaenoic acids (22:6 ω-3) using simplified phenomenological modeling. *Journal of the science of food and agriculture*, 91(8), 1452-8. doi:10.1002/jsfa.4332

Rüsch gen. Klaas, M., & Meurer, P. U. (2004). A palmitoleic acid ester concentrate from seabuckthorn pomace. *European Journal of Lipid Science and Technology*, 106(7), 412-416. doi:10.1002/ejlt.200400968

Tanabe, Y., Makita, A., Funakoshi, S., Hamasaki, R., & Kawakusu, T. (2002a). Practical Synthesis of (Z)-Civetone Utilizing Ti-Dieckmann, (5), 4-7.

Tanabe, Y., Makita, A., Funakoshi, S., Hamasaki, R., & Kawakusu, T. (2002b). Practical Synthesis of (Z)-Civetone Utilizing Ti-Dieckmann, (5), 4-7.

Tenllado, D., Reglero, G., & Torres, C. F. (2011). A combined procedure of supercritical fluid extraction and molecular distillation for the purification of alkylglycerols from shark liver oil. *Separation and Purification Technology*, 83, 74-81. Elsevier B. V. doi:10.1016/j.seppur.2011.09.013

Thomas, R. M., Keitz, B. K., Champagne, T. M., & Grubbs, R. H. (2011). Highly selective ruthenium metathesis catalysts for ethenolysis. *Journal of the American Chemical Society*, 133(19), 7490-6. doi:10.1021/ja200246e U.S. Pat. No. 6,861,551.pdf. (n.d.).

U.S. Pat. No. 7,943,560 Cyclopropane.pdf. (n.d.).

Wille, J. J., & Kydonieus, A. (2003). Palmitoleic acid isomer (C16:1delta6) in human skin sebum is effective against gram-positive bacteria. *Skin Pharmacology and Applied Skin Physiology*, 16(3), 176-187. Retrieved from http://www.ncbi.nlm.nih.gov/pubmed/12677098

Yang, B., & Kallio, H. P. (2001). Fatty acid composition of lipids in sea buckthorn (Hippophaë rhamnoides L.) berries of different origins. *Journal of agricultural and food chemistry*, 49(4), 1939-47. Retrieved from http://www.ncbi.nlm.nih.gov/pubmed/11308350

Zabeti, M., Wan Daud, W. M. A., & Aroua, M. K. (2009). Activity of solid catalysts for biodiesel production: A review. *Fuel Processing Technology*, 90(6), 770-777. Elsevier B. V. doi:10.1016/j.fuproc.2009.03.010

What is claimed is:

1. A method for synthesizing dihydrocivetone, comprising:
   a. Producing esters from an oleaginous composition comprising at least 50 mass % of palmitoleic acid and oleic acid as a percentage of the total mass of unsaturated fatty acids;
   b. Reacting at least a portion of the esters in a metathesis reaction with ethene to produce a first reaction mixture;
   c. Reacting at least a portion of the first reaction mixture in a condensation reaction to produce a second reaction mixture;
   d. Reacting at least a portion of the second reaction mixture in a metathesis reaction to produce a third reaction mixture;
   e. Hydrolyzing at least a portion of the third reaction mixture to produce a fourth reaction mixture;
   f. Decarboxylating at least a portion of the fourth reaction mixture to produce civetone; and
   g. Hydrogenating at least a portion of the civetone to produce dihydrocivetone.

2. A method of synthesizing cyclopropanated civetone, comprising:
   h. Producing esters from an oleaginous composition comprising at least 50 mass % of palmitoleic acid and oleic acid as a percentage of the total mass of unsaturated fatty acids;
   i. Reacting at least a portion of the esters in a metathesis reaction to produce a first reaction mixture;
   j. Reacting at least a portion of the first reaction mixture in a cyclization reaction to produce a second reaction mixture;
   k. Hydrolyzing at least a portion of the second reaction mixture to produce a third reaction mixture;
   l. Decarboxylating at least a portion of the third reaction mixture to produce a fourth reaction mixture comprising civetone; and
   m. Reacting at least a portion fourth reaction mixture comprising civetone in a Simmons-Smith reaction using ZnCu and $CH_2I_2$ to produce cyclopropanated civetone.

3. A method for synthesizing cyclopropanated civetone, comprising:
   n. Producing esters from an oleaginous composition comprising at least 50 mass % of palmitoleic acid and oleic acid as a percentage of the total mass of unsaturated fatty acids;
   o. Reacting at least a portion of the esters in a metathesis reaction with ethene to produce a first reaction mixture;
   p. Reacting at least a portion of the first reaction mixture in a condensation reaction to produce a second reaction mixture;
   q. Reacting at least a portion of the second reaction mixture in a metathesis reaction to produce a third reaction mixture;
   r. Hydrolyzing at least a portion of the third reaction mixture to produce a fourth reaction mixture;
   s. Decarboxylating at least a portion of the fourth reaction mixture to produce civetone; and
   t. Reacting at least a portion of the civetone in a Simmons-Smith reaction using ZnCu and $CH_2I_2$ to produce cyclopropanated civetone.

4. A method of synthesizing melanin production inhibitors C or D, comprising:
   w. Producing esters from an composition comprising at least 50 mass % of palmitoleic acid and oleic acid;
   x. Reacting at least a portion of the esters in a metathesis reaction to produce a first reaction mixture;
   y. Reacting at least a portion of the first reaction mixture in a cyclization reaction to produce a second reaction mixture;
   z. Hydrolyzing and hydrolyzing at least a portion of the second reaction mixture to produce a third reaction mixture comprising civetone; and
   aa. Reducing at least a portion third reaction mixture comprising civetone to produce a fourth reaction mixture comprising the melanin production inhibitor C or D.

5. The method of claim 4, further comprising hydrogenating the fourth reaction mixture to produce civetol.

* * * * *